United States Patent [19]

Beck et al.

[11] 4,016,169
[45] Apr. 5, 1977

[54] PROCESS FOR PREPARING TRICHLOROTHIAZOLE

[75] Inventors: Gunther Beck, Leverkusen; Dieter Arlt, Cologne, both of Germany

[73] Assignee: Bayer Aktiengesellschaft, Leverkusen, Germany

[22] Filed: Oct. 28, 1975

[21] Appl. No.: 626,416

[30] Foreign Application Priority Data

Oct. 30, 1974 Germany .......................... 2451632

[52] U.S. Cl. ........................................... 260/302 R
[51] Int. Cl.$^2$ ...................................... C07D 277/32
[58] Field of Search ............................... 260/302 R

[56] References Cited

UNITED STATES PATENTS

| | | | |
|---|---|---|---|
| 3,833,601 | 9/1974 | Beck et al. | 260/302 R |
| 3,907,819 | 9/1975 | Herkes | 260/302 R |

*Primary Examiner*—R. J. Gallagher
*Attorney, Agent, or Firm*—Burgess, Dinklage & Sprung

[57] ABSTRACT

Trichlorothiazole is prepared by reacting 1,2-dichloro-ethyl-isocyanide dichloride with a sulphur chloride at elevated temperatures in the presence of catalytic amounts of a Friedel-Crafts catalyst.

9 Claims, No Drawings

PROCESS FOR PREPARING TRICHLOROTHIAZOLE

This invention relates to a process for the preparation of trichlorothiazole.

A process for the preparation of trichlorothiazole is known (German Published Specification No. 2,213,865) wherein pentachloroethyl-isocyanide dichloride or trichlorovinyl-isocyanide dichloride is heated with sulphur, whereupon trichlorothiazole and disulphur dichloride are formed.

The known process has the disadvantage that disulphur dichloride is formed in large amounts as a by-product and that the isocyanide dichlorides employed for the reaction are only accessible in an involved manner by multi-stage syntheses and/or in poor yields.

SUMMARY

According to the present invention, trichlorothiazole is prepared by reacting 1,2-dichloroethylisocyanide dichloride with a sulphur chloride at an elevated temperature, in the presence of a catalytic amount of a Friedel-Crafts catalyst. The reaction is in general carried out in the temperature range of about 150° to 300° C, preferably in the temperature range of about 180° to 230° C.

DESCRIPTION

Disulphur dichloride and sulphur dichloride may be mentioned as sulphur chlorides which are used preferentially in the process according to the invention.

The process according to the invention can be illustrated in more detail by the following equations:

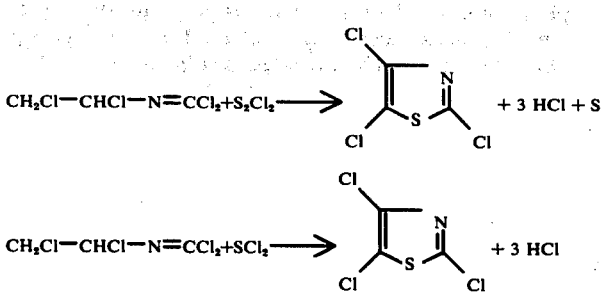

Per mol of 1,2-dichloroethyl-isocyanide dichloride, 1 mole of the sulphur chlorides $S_2Cl_2$ or $SCl_2$ are required for total conversion to trichlorothiazole. However, it has proved expedient to employ the sulphur chloride in excess in the reaction, for example in an excess of about 10 — 50% of the stoichiometrically required amount. Of course, mixtures of $S_2Cl_2$ and $SCl_2$ can also be employed.

In principle, any of the catalysts known for Friedel-Crafts reactions (compare, for example "Friedel-Crafts and Related Reactions", volume I, page 201) can be employed as the Friedel-Crafts catalyst for the process according to the invention. Examples which may be mentioned are: $AlCl_3$, $AlBr_3$, $BeAl_2$, $CdCl_2$, $ZnCl_2$, $BF_3$, $BCl_3$, $BBr_3$, $GaCl_3$, $TiCl_4$, $TiBr_4$, $ZrCl_4$, $SnCl_4$, $SnBr_4$, $SbCl_5$, $SbCl_3$, $BiCl_3$, $FeCl_3$ and $UCl_4$. $AlCl_3$, $FeCl_3$ or $ZnCl_2$ are particularly preferred. In general, about 0.01 to 10 percent by weight, preferably 0.1 to 1 percent by weight, based on 1,2-dichloroethyl-isocyanide dichloride, are employed.

The 1,2-dichloroethyl-isocyanide dichloride used as the starting material is known and can, for example, be obtained in good yield by reaction of vinyl chloride, cyanogen chloride and chlorine (Synthesis 1970, 2, 20).

The process according to the invention can be carried out, for example, by mixing 1,2-dichloroethyl-isocyanide dichloride with about 10 to 25% excess of sulphur chloride and about 0.1 to 1 percent by weight of the Friedel-Crafts catalyst and heating the mixture. In the temperature range between about 70° C (in the case of $SCl_2$) and 120° C (in the case of $S_2Cl_2$), a vigorous evolution of HCl gas starts. When this has subsided, heating of the reaction mixture under reflux is continued until the conversion to the desired product has virtually been completed, and in the course of this the temperature of the reaction mixture is gradually raised to about 205° – 225° C. The end point of the reaction can be ascertained in a simple manner by IR spectroscopy, from the disappearance of the absorption in the region between 1,600 and 1,650 $cm^{-1}$ which is characteristic of all isocyanide-dichlorides.

The time required to reach practically complete conversion naturally depends on the molar ratios or weight ratios used, on the temperature course, and the like. It is within the range from about one hour and about a hundred hours. Experience has shown that conversion to trichlorothiazole is over 90% after as little as about one quarter to one half of the total reaction time, that is to say when the internal temperature has reached its particular maximum value, so that it can be of advantage to discontinue the reaction at that point in time and work up the mixture by fractional distillation. Of course, the process can also be carried out continuously.

The insecticidal properties of trichlorothiazole are known (see German Published Specification No. 2,213,865).

Compared to the known processes of preparation of trichloroiazole according to German Published Specification No. 2,213,865, the process according to the invention has the advantage that no disulphur dichloride is formed by a by-product. Furthermore, the 1,2-dichloroethyl-isocyanide dichloride which is used for the process according to the invention is accessible in very good yield and in a one-stage reaction from inexpensive starting materials.

The following examples are given by way of illustration only:

EXAMPLE 1

A mixture of 390 g (2 mols) of 1,2-dichloroethylisocyanide dichloride, 300 g (2.22 mols) of disulphur dichloride and about 1 g of aluminium chloride is first heated to about 120° – 125° C, until the evolution of HCl gas has subsided. The heating bath temperature is then gradually raised in such a way that on the one hand the evolution of HCl gas does not become too vigorous, whilst on the other hand the heating bath temperature is constantly kept about 40° to 70° C above the reflux temperature of the reaction mixture, which gradually rises in the course of the reaction. Heating is continued at least until the boiling point of the mixture no longer rises. The reaction has ended when the IR spectrum of a sample no longer shows an absorption between 1,600 and 1,650 c,$^{-1}$. The final temperature is about 220° C (oil bath temperature 250° – 265° C) and the time required for virtually complete disappearance of the IR band at between 1,600 and 1,650 cm$^{-1}$ is about 40 to 50 hours. The reaction mixture is then thoroughly distilled in a waterpump vacuum until the bath temperature reaches about 250° C (about 300 g of distillate and about 100 g of residue), and thereafter the distillate is again fractionated, using a column. At 75 to 79° C/12 mm Hg, 280 g of trichlorothiazole are obtained in a purity, determined by gas chromatography, of about 99%. Yield, 73.5% of theory.

The five main bands in the IR spectrum of trichlorothiazole are at least 1,488, 1,423, 1,225, 1,060 and 870 cm$^{-1}$.

EXAMPLE 2

A mixture of 390 g (2 mols) of 1,2-dichloroethyl-isocyanide dichloride, 260 g (2.5 mols) of sulphur dichloride and about 1.5 g of aluminium chloride is first heated to about 70° to 75° C, until the evolution of HCl gas has subsided. Thereafter, the procedure described in Example 1 is followed. The maximum internal temperature of about 210° C is reached after as little as about 20 hours. The IR spectrum of the reaction mixture at that point in time shows no more than a slight absorption between 1,600 and 1,650 cm$^{-1}$, compared to the bands of the trichlorothiazole, corresponding to a conversion of more than 90%. The mixture is then heated for a further 40 to 50 hours under reflux (about 210° C) until the isocyanide dichloride band has virtually completely disappeared.

The mixture is worked up as in Example 1, whereby first a distillate of about 320 g (residue 40 g) is obtained, which on fractional distillation gives 300 g of trichlorothiazole in a purity, determined by gas chromatography, of more than 99%, corresponding to a yield of 79% of theory.

What is claimed is:
1. Process for preparing trichlorothiazole, which comprises reacting 1,2-dichloroethyl-isocyanide dichloride with a sulphur chloride selected from the group consisting of disulphur dichloride and sulphur dichloride at elevated temperatures in the presence of catalytic amounts of a Friedel-Crafts catalyst.
2. Process of claim 1 carried out at temperatures of 150° – 300° C.
3. Process of claim 1 carried out at temperatures of 180° – 230° C.
4. Process of claim 1 wherein the reaction is carried out with at least the stoichiometrically required amount of sulphur chlorides.
5. Process of claim 1 wherein the Friedel-Crafts catalyst is employed in an amount of 0.01 to 10 percent by weight.
6. Process of claim 1 wherein the Friedel-Crafts catalyst is employed in an amount of 0.1 to 1 percent by weight.
7. Process of claim 1 wherein aluminum chloride, iron (III) chloride or zinc chloride is employed as the Friedel-Crafts catalyst.
8. A process according to claim 1 wherein the sulphur chloride which is reacted is disulphur dichloride.
9. A process according to claim 1 wherein the sulphur chloride which is reacted is sulphur dichloride.

* * * * *

UNITED STATES PATENT AND TRADEMARK OFFICE
CERTIFICATE OF CORRECTION

PATENT NO. : 4,016,169
DATED : April 5, 1977
INVENTOR(S) : Gunther Beck et al.

It is certified that error appears in the above—identified patent and that said Letters Patent are hereby corrected as shown below:

Column 2, line 57, change "by" first occurrence to -- as --.

Column 3, line 11, change "1,650 c,$^{-1}$" to -- 1,650 cm$^{-1}$ --.

Column 3, line 25, delete "least" after "at".

Signed and Sealed this

Twenty-first Day of June 1977

[SEAL]

Attest:

RUTH C. MASON
Attesting Officer

C. MARSHALL DANN
Commissioner of Patents and Trademarks